United States Patent [19]

Stohrer et al.

[11] Patent Number: 5,605,649

[45] Date of Patent: Feb. 25, 1997

[54] POLYMERIZABLE LIQUID-CRYSTALLINE SILOXANES

[75] Inventors: Juergen Stohrer, Munich; Willibald Lottner, Weilheim, both of Germany

[73] Assignee: Consortium fur elektrochemische Industrie GmbH, Munich, Germany

[21] Appl. No.: 362,390

[22] Filed: Dec. 22, 1994

[30] Foreign Application Priority Data

Dec. 23, 1993 [DE] Germany .................. 43 44 308.7

[51] Int. Cl.$^6$ .................. C09K 19/52; G02F 1/1335
[52] U.S. Cl. .................. 252/299.01; 252/299.62; 252/299.64; 252/299.66; 428/1; 349/104; 349/113
[58] Field of Search .................. 252/299.01, 299.62, 252/299.64, 299.66; 359/66, 70; 428/1

[56] References Cited

U.S. PATENT DOCUMENTS

| | | | |
|---|---|---|---|
| 4,388,453 | 6/1983 | Finkelmann et al. | 252/299.01 |
| 5,185,419 | 2/1993 | Funk et al. | 528/25 |
| 5,211,877 | 5/1993 | Andrejewski et al. | 252/299.01 |
| 5,399,290 | 3/1995 | Häberle et al. | 252/299.01 |
| 5,455,697 | 10/1995 | Coles et al. | 252/299.01 |
| 5,486,311 | 1/1996 | Hsiue et al. | 252/299.66 |
| 5,498,368 | 3/1996 | Coles et al. | 252/299.67 |

FOREIGN PATENT DOCUMENTS

| | | |
|---|---|---|
| 0358208 | 3/1990 | European Pat. Off. . |
| 0442097 | 8/1991 | European Pat. Off. . |
| 0471277 | 2/1992 | European Pat. Off. . |
| WO93/05436 | 3/1993 | WIPO . |

OTHER PUBLICATIONS

Rivas, "Synthesis and properties of compounds with two different terminal mesogenic units and tetramethyldisiloxane as spacer" Bol. Soc. Chil. Quin., vol. 32(3), pp. 143–153, 1987.

*Primary Examiner*—Shean C. Wu
*Attorney, Agent, or Firm*—Martin Connaughton

[57] ABSTRACT

Polymerizable liquid-crystalline siloxanes of a defined composition which are distinguished by low viscosity and pronounced thermochromic properties. The liquid-crystalline siloxanes of the present invention are used for the production of membranes in the optical display of electromagnetic field, opto-electronics, information storage and in particular in the production of optical filters and reflectors.

7 Claims, No Drawings

POLYMERIZABLE LIQUID-CRYSTALLINE SILOXANES

FIELD OF INVENTION

The present invention relates to fully polymerizable liquid-crystalline siloxanes, to a process for their preparation, to their use, and to liquid-crystalline polyorganosiloxanes obtainable by polymerization of the liquid-crystalline siloxanes.

BACKGROUND OF THE INVENTION

Polymerizable, liquid-crystalline polysiloxanes and processes for their preparation are disclosed, for example, in U.S. Pat. No. 4,388,453 and U.S. Pat. No. 5,211,877. However, on polymerization the polysiloxanes described therein form polymers which are three-dimensionally crosslinked and are therefore brittle and fracture easily. Furthermore, the polysiloxanes described therein have high viscosity, i.e., can only be processed at elevated temperatures, which in turn can result in premature partial polymerization of the materials. At lower temperatures, the establishment of equilibrium states, such as alignment, is hindered by the high viscosity.

Owing to the preparation processes described therein, the oligomeric and polymeric compounds described are not defined homogeneous compounds, but instead are always statistical mixtures of siloxanes having different substitution patterns. This can result in nonhomogeneous or heterogeneous phases, which cannot be used for optical applications. Furthermore, these mixtures generally cannot be polymerized fully, since non-polymerizable siloxanes are present in various amounts. These mixtures generally cannot be crystallized, which makes simple purification of the siloxanes more difficult.

The known polymerizable liquid-crystalline polysiloxanes, if they have a cholesteric phase, have only low temperature dependence of the color of the cholesteric reflection within the temperature range available for processing, i.e., they exhibit only weak thermochromic properties. For use in photolithographically structurable filters, however, pronounced thermochromic properties are an absolute necessity.

Polymerizable polysiloxanes containing mesogenic groups are also disclosed in EP-A-471 277. However, the monomeric siloxanes described therein usually only form crystalline or liquid phases. Only in a few cases are highly ordered liquid-crystalline phases obtained. However, highly ordered liquid-crystalline phases are distinguished by high viscosity and can therefore only be processed in solution or the melt with loss of their liquid-crystalline property and/or at high temperatures, which can result in premature polymerization of the materials. Furthermore, highly ordered phases cannot be applied and aligned by simple methods such as knife coating or spin coating. In addition, highly ordered phases do not have colored reflection and therefore do not have thermochromic properties either.

SUMMARY OF INVENTION

The object of the present invention was to find polymerizable liquid-crystalline siloxanes of defined composition which are distinguished by low viscosity, and to provide a process for their preparation. A further object was to find polymerizable liquid-crystalline siloxanes having pronounced thermochromic properties.

The present invention relates to liquid-crystalline siloxanes of the formula

in which
Y$^1$ is an alkyl or alkenyl radical containing a mesogenic group,
Y$^2$ is an organic radical containing at least one polymerizable group and at least one divalent cyclic group,
R is a C$_1$- to C$_3$-alkyl radical, and
$\pi$ is an integer having a value of from 1 to 5.

The term "mesogenic groups" is well known to persons skilled in the art. These are groups which can cause liquid-crystalline properties in a molecule. Examples of mesogenic groups are derivatives of cyclohexane, such as cyclohexyl cyclohexanecarboxylate, phenyl cyclohexanecarboxylate, cyclohexyl phenyl ether, cyclohexylbenzenes, dicyclohexyl derivatives, derivatives of stilbene, phenyl benzoate and its derivatives, steroids, such as cholesterol, cholestan, doristerol and derivatives thereof, such as cholesterol esters, benzylideneanilines, azobenzene and derivatives thereof, azoxybenzene and derivatives thereof, alkyl and alkoxy derivatives of biphenyl, and Schiff bases. It is frequently desired, for applicational reasons, for the mesogenic groups to contain polar functions, such as the nitrile group, in order to achieve a high dielectric anisotropy effect in the liquid crystal.

Preferred alkenyl and alkyl radicals Y$^1$ containing mesogenic groups are those of the formula

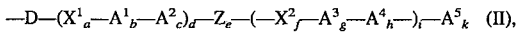

in which
D is a divalent hydrocarbon radical of the formula C$_n$H$_m$ which is unsubstituted or substituted by halogen atoms and in which one or more non-adjacent methylene units may be replaced by X$^1$,
n is an integer having a value of from 0 to 20
m is a non-negative number having a value of (2n) or (2n-2),
X$^1$ and X$^2$ are each divalent radicals from the group consisting of —O—, —COO—, —CONH—, —CO—, —S—, —C≡C—, —CH=CH—, —CH$_2$—CH$_2$—, —CH=N—, —N=N— and —N=N(O)—,
A$^1$, A$^2$, A$^3$ and A$^4$ are each divalent radicals, namely 1,4-phenylene, 1,4-cyclohexylene radicals, substituted arylenes having 1 to 10 carbon atoms, substituted cycloalkylenes having 1 to 10 carbon atoms and heteroarylene having 1 to 10 carbon atoms,
Z are each divalent to tetravalent benzene-1,4-cyclohexane or 1,3-cyclopentane radicals,
A$^5$ are each saturated or olefinically unsaturated alkyl, alkoxy or cycloalkyl radicals having 1 to 16 carbon atoms, steroid radicals, halogen atoms, hydrogen atoms, hydroxyl, nitrile and trialkylsiloxy groups whose respective alkyl radicals have 1 to 8 carbon atoms,
a, b, c, d, f, g, h, i and k are each independent of each other, integers having a value of 0, 1, 2 or 3, the sum a+b+c+d+e+f+g+h+i+k is at least 2 and the sum of d and i is at most 4, and
e is a number having a value of 0 or 1,
with the proviso that no two oxygen atoms in Y$^1$ are directly bonded to one another.

The radicals X$^1$ and X$^2$ can, if they do not have a symmetrical structure, be bonded at both ends to each of their bonding partners. Thus, for example, the radical —COO— can also be bonded as —OOC—, the radical —CONH— as —NHCO—, and —CH=N— as —N=CH— in the above formula (II) and in the formulae mentioned below.

Preferred substituents for the substituted arylenes and cycloalkylenes $A^1$, $A^2$, $A^3$ and $A^4$ are halogen atoms, $C_1$ to $C_4$-alkoxy radicals, nitro and cyano groups, $C_1$- to $C_6$-alkyl radicals, carboxy-($C_1$- to $C_4$-alkyl) radicals and tri($C_1$ to $C_4$-alkyl)siloxy radicals.

n preferably has a value of from 3 to 6, m preferably has the value 2n, k preferably has the value of 1, a and f have each independent of each other preferably the value of 0 or 1.

Examples of radicals $A^5$ are alkyl radicals, such as methyl, ethyl, n-propyl, iso-propyl, n-butyl, iso-butyl, tert-butyl, n-pentyl, iso-pentyl, neo-pentyl and tert-pentyl radicals, hexyl radicals, such as the n-hexyl radical, heptyl radicals, such as the n-heptyl radical, octyl radicals, such as the n-octyl radical, and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, hexadecyl radicals, such as the n-hexadecyl radical; alkenyl radicals, such as the vinyl and allyl radicals, butenyl, pentenyl, hexenyl, heptenyl, octenyl, octadienyl, decenyl, dodecenyl and hexadecenyl radicals; cycloalkyl radicals, such as cyclopentyl, cyclohexyl, cycloheptyl and methylcyclohexyl radicals; alkoxy radicals, such as the methoxy, ethoxy, n-propoxy, iso-propoxy, n-, sec- and tert-butoxy, pentoxy, hexoxy, octoxy, decoxy and hexadecoxy radicals, alkenoxy radicals, such as the allyloxy, butenyloxy, pentenyloxy, hexenyloxy, octenyloxy, decenyloxy and hexadecenyloxy radicals; cycloalkyl radicals, such as the cyclopentyl, cyclohexyl and cycloheptyl radicals; cycloalkenyl radicals, such as cyclopentenyl, cyclohexenyl and cycloheptenyl radicals; steroid radicals, such as the cholestan, cholesteryl and doristeryl radicals; fluorine, chlorine or bromine atoms; hydrogen atoms; hydroxyl, nitrile, trimethylsilyloxy and triethylsilyloxy groups.

—D—$(X^1_a$—$A^1_b$—$A^2_c)_d$— in formula (II) is preferably a radical of the formula

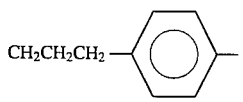 (III)

Preferred compounds of formula (II) are those of the formula

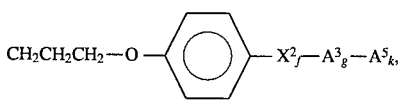 (IV)

in which $X^2$, $A^3$, $A^5$, f, g and k are as defined for formula (II), f preferably having the value of 1, g preferably having the value of 0 or 1 and k preferably having the value of 1.

Preferred organic radicals $Y^2$ containing at least one polymerizable group and at least one divalent cyclic group are those of the formula

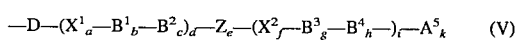 (V)

in which $B^1$, $B^2$, $B^3$ and $B^4$ are as defined for the radicals $A^1$, $A^2$, $A^3$, $A^4$ and D, D, $X^1$, $X^2$, Z, $A^5$, a, b, c, d, f, g, h, i, k and e are as defined above under formula II, where the sum b+c+e+g+h is at least 1, with the proviso that no two oxygen atoms in $Y^2$ are directly bonded to one another and at least one ethylenically unsaturated double bond is present.

The radical $Y^2$ preferably contains at least one (meth)acrylyl, vinyl or cinnamic acid ester group.

Preferred organic radicals $Y^2$ containing at least one polymerizable group and at least one divalent cyclic group are the readily photopolymerizable radicals of the formula

—$(CH_2)_s$—$(X^1)_t$—$(A^1)_u$—$R^1$ (VI), in which $R^1$ is a radical from the group consisting of the compounds of the formulae

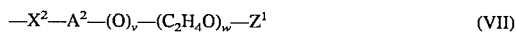
—$X^2$—$A^2$—$(O)_v$—$(C_2H_4O)_w$—$Z^1$ (VII)

and

—$Z^2$—$A^2$—$A^5$ (VIII), in which s is an integer having a value of from 2 to 8, t, u and v are each 0 or 1, w is an integer having a value of 0, 1 or 2, $Z^1$ is a (meth)acrylyl or vinyl group, $Z^2$ is a group of the formula —CH=CH—COO— or —OOC—CH=CH—, and $A^1$, $A^2$, $A^5$, $X^1$ and $X^2$ are as defined above In formulae (VI) to (VIII), $A^1$ and $A^2$ are preferably 1,4-phenylene radicals. $Z^1$ is preferably a methacrylyl group. w is preferably 0, and v is preferably 1.

Examples of the radical R are the methyl, ethyl, n-propyl and i-propyl radicals, the methyl radical being preferred.

π preferably has the value of 1.

The liquid-crystalline siloxanes of formula (I) according to the invention can be prepared by the following process:

In a first step,

α,ω-dihydrosiloxane of the formula

H—$(SiR_2$—$O)_\pi$—$SiR_2$—H (IX), is reacted with an alkene and/or alkyne containing mesogenic groups in the presence of a known hydrosilylation catalyst to give a compound of the formula

$Y^1(SiR_2O)_\pi$—$SiR_2H$ (X), where $Y^1$, R and π in formulae (IX) and (X) are as defined above.

The reaction is preferably carried out in a 0.5 to 100 fold, in particular 5 to 20 fold, excess of the compound of formula (IX) with respect to the alkene and/or alkyne containing mesogenic groups, if desired in the presence of a solvent, preferably in the presence of 1 to 5000 ppm, in particular 10 to 100 ppm, of a hydrosilylation catalyst, preferably at temperatures of 20° C. to 120° C., in particular 50° C. to 80° C., preferably under a pressure of 0.05 to 1 MPa, in particular 0.09 to 0.2 MPa. The excess compound of formula (IX) is preferably removed from the reaction mixture by distillation, preferably at a temperature of 20° C. to 140° C., in particular 20° C. to 100° C., and preferably at a pressure of 0.001 to 100 kPa, in particular 1 to 10 kPa. In an alternative method, the excess of the compound of formula (IX) can also be removed by precipitation of the reaction product of formula (X) by addition of suitable solvents and separation of the liquid phase from the reaction product.

In a second step, the reaction product of formula (X) is reacted with an alkene and/or alkyne containing at least one polymerizable group and at least one divalent cyclic group in the presence of a known hydrosilylation catalyst to give a compound of formula (I).

The preferred siloxanes according to the invention containing radicals of formula (V) are preferably prepared by reacting a compound of formula (X) with a compound of the formula

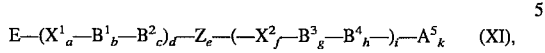

$$E-(X^1_a-B^1_b-B^2_c)_d-Z_e-(-X^2_f-B^3_g-B^4_h-)_i-A^5_k \quad (XI),$$

in which

E is a monovalent hydrocarbon radical of the formula $C_nH_{(m-1)}$ which is unsubstituted or substituted by halogen atoms and in which one or more non-adjacent methylene units may be replaced by $X^1$, and $X^1$, $X^2$, $B^1$, $B^2$, $B^3$, $B^4$, Z, $A^5$, a, b, c, d, e, f, g, h, i and k are as defined above.

In the reaction, a ratio of 0.5 to 1.5, in particular 0.8 to 1.1, is preferably selected between the compound of formula (X) and the alkene and/or alkyne containing a polymerizable group and at least one divalent cyclic group. The reaction is carried out in the presence or absence of a solvent, preferably at temperatures of 20° C. to 120° C., in particular 50° C. to 100° C., and preferably under a pressure of 0.05 to 1 MPa, in particular 0.09 to 0.2 MPa. In an alternative method, this reaction can be carried out using an alkene and/or alkyne which contains at least one divalent cyclic group and which has been provided with a protecting group, wherein the protecting group is removed in the third step in a known manner and a polymerizable group is attached in a suitable manner. In an alternative method, an alkene and/or alkyne which contains at least one divalent cyclic group and is provided with a protecting group is employed in the first step and an alkene and/or alkyne provided with a mesogenic group is employed in the second step.

The hydrosilylation catalyst used in both steps can be the same catalyst, but it is also possible to add an additional catalyst in the second step. The novel reaction both of the alkenes and/or alkynes containing mesogenic groups and of the alkenes and/or alkynes containing at least one polymerizable group or protecting group with directly silicon-bonded hydrogen atoms of the siloxanes of formulae (X) and (XI) is preferably carried out in the presence of a hydrosilylation catalyst containing ruthenium, rhodium, palladium, platinum and/or compounds thereof. Preference is given to platinum and/or compounds thereof. All catalysts can be employed here which have hitherto been employed for the addition reaction of directly silicon-bonded hydrogen atoms with aliphatically unsaturated compounds. Examples of such catalysts are metallic and finely divided platinum, which can be on supports, such as silicon dioxide, aluminum oxide or activated charcoal, compounds or complexes of platinum, such as platinum halides, for example $PtCl_4$, $H_2PtCl_6 \cdot 6H_2O$, $Na_2PtCl_4 \cdot 4H_2O$, platinum-olefinic complexes, platinum-alcohol complexes, platinum-alkoxide complexes, platinum-ether complexes, platinum-aldehyde complexes, platinum-ketone complexes, including products of the reaction of $H_2PtCl_6 \cdot 6H_2O$ and cyclohexanone, platinum-vinylsiloxane complexes, in particular platinum-divinyltetramethyldisiloxane complexes containing or not containing detectable inorganically bonded halogen, bis (γ-picolinyl)platinum dichloride, trimethylenedipyridinylplatinum dichloride, dicyclopentadienylplatinum dichloride, (dimethyl sulfoxide)ethyleneplatinum(II) dichloride and products of the reaction of platinum tetrachloride with olefin and primary amine or secondary amine or primary and secondary amine, such as the product of the reaction of platinum tetrachloride dissolved in 1-octene with sec-butylamine, or ammonium-platinum complexes.

If solvents are used, preference is given to solvents or solvent mixtures which are substantially inert under the reaction conditions and in particular those having a boiling point or boiling range of up to 120° C. at 0.1 MPa. Examples of such solvents are ethers, such as dioxane, tetrahydrofuran, diethyl ether, methyl tert-butyl ether, diethylene glycol dimethyl ether; chlorinated hydrocarbons, such as dichloromethane, trichloromethane, tetrachloromethane, 1,2-dichloroethane, trichloroethylene; hydrocarbons, such as pentane, n-hexane, hexane isomer mixtures, heptane, octane, white spirit, petroleum ether, benzene, toluene, xylenes; ketones, such as acetone, methyl ethyl ketone, methyl isobutyl ketone; esters, such as ethyl acetate, methyl acetate, n-butyl acetate, ethyl formate; carbon disulfide and nitrobenzene, or mixtures of these solvents. The term solvent does not mean that all reaction components must dissolve therein. The reaction can also be carried out in a suspension or emulsion of one or more reactants. The reaction can also be carried out in a solvent mixture having a miscibility gap, in which case at least one of the reactants is soluble in each of the mixed phases.

Examples of protecting groups for hydroxyl groups are described in U.S. Pat. No. 5,211,877. Thus, the hydrogen atom of the hydroxyl group can be replaced, for example, by a tert-butyl, benzyl, triphenylmethyl, trialkylsilyl, formaldehyde acetal, acetaldehyde acetal, O,N-acetal, O,O-acetal, carboxylate, such as chloroacetate, orthoester or carbonate group. The chemical nature of the protecting group is relatively unimportant in the process according to the invention. The crucial factor is that the protecting group is stable during the additional reaction of the alkene and/or alkyne onto hydrogens bonded directly to silicon, but can be removed after this reaction under conditions under which the product is essentially inert.

Preference is given to acid-labile protecting groups, in particular the tri($C_1$- to $C_4$-alkyl)silyl, tert-butyl, triphenylmethyl and orthoformate groups, particularly the trimethylsilyl group. The removal of the protecting group and introduction of a polymerizable groups are carried out in a manner known, for example, as described in U.S. Pat. No. 5,211,877.

All the reactants, catalysts, solvents, photo-initiators and devices such as UV light sources mentioned above or below can be employed individually or as mixtures. For example, it is possible to employ in each case one compound of formula (I) or (IX) and (X), a platinum catalyst, a solvent, etc., but it is also possible to employ mixture or combinations of each of the substances or equipment mentioned above.

The compounds of formula (I) according to the invention can, in order to modify their thermal properties and their polymerization properties, be mixed with other compounds, such as low-molecular-weight, mesogenic or non mesogenic compounds in order to reduce the viscosity, photoinitiators and photosensitizers for UV photocrosslinking, polymerization inhibitors for preventing premature polymerization, as described in U.S. Pat. No. 5,211,877. Fillers can likewise be used in the manner described in U.S. Pat. No. 5,211,877.

The siloxanes according to the invention are particularly suitable for photopolymerization. The siloxanes are preferably polymerized by applying them to a substrate at temperatures of from −20° C. to 160° C., in particular from 20° C. to 140° C., and aligning them in a manner known, for example by melt application by means of a knife coater, by electric or magnetic fields or by application to substrates provided with alignment layers, and subsequently exposing them to the radiation from a UV lamp at the same or another temperature. The liquid-crystalline polyorganosiloxanes obtainable by polymerization of the siloxanes according to the invention likewise represent a subject-matter of the invention.

The liquid-crystalline siloxanes according to the invention are used for the production of membranes, in particular for the separation of substance mixtures, for example of gases, such as oxygen and nitrogen, in the optical display of electromagnetic fields, optoelectronics, in the area of information storage, electrographic methods, light modulation, as a constituent or polarizing foils, optical filters and reflectors, in coatings, as a security feature, for example on bank notes and check cards, as a constituent of paint pigments and as stationary phases for gas and liquid chromatography. They are particularly suitable for the production of optical filters and reflectors.

Siloxanes according to the invention can, so long as they have a cholesteric phase, also be used in a manner known for the production of photostructurable, optical materials, such as filters. To this end, these substances are shaped as films, brought to the desired temperature in order in this way to establish the desired optical property of the film, such as the color of the light reflected by the film, and then photopolymerized, if desired by means of a mask, in order permanently to fix the established properties of the film in the desired regions. This operation can, if desired, be repeated using various masks in order to obtain multicolored, structured filters and reflectors.

In the examples described below, unless otherwise stated,
(a) all amounts are by weight,
(b) all pressures are 0.10 MPa (abs.)
(c) all temperatures are 20° C.
Phase abbreviations:
c=crystalline,
g=glassy,
i=isotropic liquid,
n*=cholesteric,
Sg=smectic G,
Sa=smectic A,
Sx=smectic.

The liquid-crystalline disiloxanes below have the structural formula

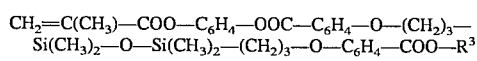

where
$R^3$=cholesteryl in Examples 1a, 2 and 3,
$R^3$=dihydrocholesteryl in Example 1b,
$R^3$=$C_6H_4$—O—$CH_3$ in Example 1c and
$R^3$=doristeryl in Example 1d.

In Example 5, the liquid-crystalline disiloxane has the structural formula

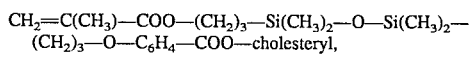

EXAMPLE 1

Fully polymerizable liquid-crystalline disiloxanes (a) 0.13 mole of cholesteryl 4-allyloxybenzoate were dissolved in 200 ml of anhydrous toluene. After 1.3 mole of 1,1,3,3-tetramethyldisiloxane had been added, 50 ppm of platinum-divinyldisiloxane complex (OL catalyst from Wacker-Chemie GmbH, Munich) were added to the homogeneous solution, which was then heated to reflux (81° C.). After 6 hours, the excess tetramethyldisiloxane and toluene were removed by distillation, and the residue was taken up twice in toluene and dried by distillation. The cholesteryl 4-(1,1,3,3-tetramethyldisiloxanyl)-propoxy)benzoate which remained was dissolved in 150 ml of anhydrous toluene, and a ion 0.12 mole of 4-methacryloxyphenyl 4-allyl in 200 ml of anhydrous toluene was added at 20° C. solution was warmed at 60° C. for 1 hour with stirring. The toluene solution of the product was evaporated, and the product was recrystallized from a mixture of acetone/water (95:5 at low temperature (0° C.). Repeated reprecipitation gave a crystalline, white compound. The following phase behavior was determined on this compound: c 85 n* 148 i 148 n* 16 g The supercooling observed in the cholesteric phase was retained from 3 to 4 days at 20° C. Aligned samples of the product had a cholesteric reflection at 400 nm at 70° C. By warming by 20 K, the reflection wave Length was shifted to 380 nm. The viscosity of this compound was 0.76 Pas at 90° C.

By comparison, the polymerizable oligomers described in U.S. Pat. No. 5,211,877, Example 1a, had a viscosity of 12 Pas at 90° C.; the reflection wavelength of 510 nm did not change on warming by 20 K.

(b) 0.13 mole of dihydrocholesteryl 4-allyloxybenzoate were dissolved in 200 ml of anhydrous toluene. After 1.3 mole of 1,1,3,3-tetramethyldisiloxane had been added, 50 ppm of platinum-divinyldisiloxane complex (CL catalyst from Wacker-Chemie GmbH, Munich) were added to the homogeneous solution, which was then heated to reflux (81° C.). After 6 hours, the excess tetramethyldisiloxane and toluene were removed by distillation, and the residue was taken up twice in toluene and dried by distillation. The dihydrocholesteryl 4-(3-(1,1,3,3-tetramethyldisiloxanyl)propoxy)benzoate which remained was dissolved in 150 ml of anhydrous toluene, and a solution 0.12 mole of 4-methacryloxyphenyl 4-allyloxybenzoate in 200 ml of anhydrous toluene was added at 20° C. The solution was warmed at 60° C. for 1 hour with stirring. The toluene solution of the product was evaporated, and the product was recrystallized from a mixture of acetone/water (95:5) at low temperature (0° C.). Repeated reprecipitation gave a crystalline, white compound. The following phase behavior was determined on this compound: c 82 n* 139 i 139 n* 15 g The supercooling observed in the cholesteric phase was retained for 3 to 4 days at 20° C. Aligned samples of the product had a cholesteric reflection at 810 nm at 70° C. By warming by 20 K, the reflection wavelength was shifted to 760 nm.

(c) 41.3 g (0.145 mole) of 4-methoxyphenyl 4-allyloxybenzoate were dissolved in 200 ml of anhydrous toluene. After 391 g (2.9 mole) of 1,1,3,3-tetramethyldisiloxane had been added, 55 ppm of platinum-divinyldisiloxane complex (OL catalyst from Wacker-Chemie GmbH, Munich) were added to the homogeneous solution, which was heated to reflux. After 6 hours, the excess tetramethyldisiloxane and toluene were removed by distillation, and the residue was taken up twice in toluene and dried by distillation. The 4-methoxyphenyl 4-(3-(1,1,3,3-tetramethyldisiloxanyl)propoxy)benzoate which remained was dissolved in 150 ml of anhydrous toluene, and a solution of 44.2 g (0.13 mole) of 4-methacryloxyphenyl 4-allyloxybenzoate in 200 ml of anhydrous toluene was added at 20° C. The solution was warmed at 60° C. for 1 hour with stirring. The toluene solution of the product was evaporated, and the product was precipitated by means of petroleum ether at low temperature (0° C.). The following phase behavior was determined on this compound: g -8 n 32 i (d) 0.13 mole of doristeryl 4-allyloxybenzoate were dissolved in 200 ml of anhydrous toluene. After 1.3 mole of 1,1,3,3-tetramethyldisiloxane had been added, 50 ppm of platinum-divinyldisiloxane complex (OL catalyst from Wacker-Chemie GmbH, Munich) were added to the homogeneous solution, which was then heated to reflux (81° C.). After 6 hours, the excess tetramethyldisiloxane and toluene were removed by distillation, and the residue was taken up twice in toluene and dried by distillation. The doristeryl 4-(3-(1,1,3,3-tetramethyldisiloxanyl)propoxy)benzoate which remained was dissolved in 150 ml of anhydrous toluene, and a solution 0.12 mole of 4-methacryloxypheny 4-allyloxybenzoate in 200 ml of anhydrous toluene was added at 20° C. The solution was warmed at 60° C. for 1 hour with stirring. The toluene solution of the product was evaporated, and the product was recrystallized from a mixture of acetone/water (95:5) at low temperature (0° C.). The following phase behavior was determined on this compound: g 25 n, 85 i The viscosity and alignment behavior are similar to the product of Example 1a.

COMPARATIVE EXAMPLE 2

Method for the preparation of fully polymerizable liquid-crystalline disiloxanes by stoichiometric reaction 0.13 mole of cholesteryl 4-allyloxybenzoate and 0.12 mole of 4-methacryloxyphenyl 4-allyloxybenzoate were dissolved in 400 ml of anhydrous toluene. After 0.16 mole of 1,1,3,3-tetramethyldisiloxane had been added, 50 ppm of platinum-divinyldisiloxane complex (OL catalyst from Wacker-Chemie GmbH, Munich) were added to the homogeneous solution, which was then heated to 80° C. After 6 hours, the $^1$H-NMR spectra showed that a conversion of less than 10% had occurred. Repeated addition of 0.1 mole portions of 1,1,3,3-tetramethyldisiloxane over a total of 24 hours gave a conversion of 90%, based on the vinyl double bond of the starting materials. The product was obtained by evaporating the toluene solution and, from chromatographic analysis, proved to be a mixture of three different products and of the starting materials, including about 30% of the desired product. Aligned samples of the material had pronounced haze, which was found under the polarizing microscope to be due to separation or multiple phases. This material is therefore not suitable for the production of optical components.

EXAMPLE 3

Preparation of fully polymerizable liquid-crystalline disiloxanes by means of a protecting group 0.13 mole of cholesteryl 4-allyloxybenzoate was dissolved in 200 ml of anhydrous toluene. After 1.3 mole of 1,1,3,3-tetramethyldisiloxane had been added, 50 ppm of platinum-divinyldisiloxane complex (OL catalyst from Wacker-Chemie GmbH, Munich) were added to the homogeneous solution, which was then heated to reflux (81° C.). After 6 hours, the excess tetramethyldisiloxane and toluene were removed by distillation, and the residue was taken up twice in toluene and dried by distillation. The cholesteryl 4-(3-(1,1,3,3-tetramethyldisiloxanyl)-propoxy)benzoate which remained was dissolved in 150 ml of anhydrous toluene, and a solution of 0.12 mole of 4-trimethylsiloxyphenyl 4-allyloxybenzoate in 150 ml of anhydrous toluene was added at 20° C. The solution was warmed at 60° C. for 1 hour with stirring. The toluene solution of the product was concentrated by evaporation and taken up in 100 ml of methyl t-butyl ether, 1 ml of 2% strength hydrochloric acid was added in order to remove the trimethylsilyl protecting group, and the mixture was kept at 80° C. for 60 minutes. The water phase was separated off, and the acid remaining in the organic phase was removed by filtration through solid sodium hydrogencarbonate. The solution which remained was freed from residual water by azeotropic distillation of the solvent. After cooling to 0° C., the solution was treated first with 0.13 mole of triethylamine and then, slowly with stirring, with 0.13 mole of methacrylyl chloride. After 1 hour, the suspension was warmed to room temperature, stirred for a further 2 hours and then freed from precipitated triethylamine hydrochloride by filtration. After the solution had been washed with 10% strength sodium chloride solution and 5% strength NaHCO$_3$ solution and the solvent had been removed by distillation, the product was precipitated from acetone at low temperature. The liquid crystal obtained in this way had the characteristic selective reflection of a cholesteric phase.

EXAMPLE 4

Polymerization example

The polymerizable disiloxane of Example 1a was mixed homogeneously with 2% by weight of a photoinitiator (Irgacure 907 from Ciba-Geigy AG, Switzerland). The mixture was aligned at 40° C. between two glass plates by applying shear forces and exposed for 30 seconds to UV light (300–360 nm, 5 mW/cm$^2$). The polymer obtained in this way had a glass transition temperature of 48° C. The clearing point was 184° C., and the sample still exhibited birefringence at up to 200° C. After the polymerization, the sample only had a very slight temperature dependence of the reflection wavelength (+0.2 nm/K; by contrast, the unpolymerized sample had an inverse temperature dependence of −1.9 nm/K).

COMPARATIVE EXAMPLE 5

Polymerizable liquid-crystalline disiloxanes containing no divalent cyclic group between the siloxane unit and the methacrylate group 0.13 mole of cholesteryl 4-allyloxybenzoate were dissolved in 200 ml of anhydrous toluene. After 1.3 mole of 1,1,3,3-tetramethyldisiloxane had been added, 50 ppm of platinum-divinyldisiloxane complex (OL catalyst from Wacker-Chemie GmbH, Munich) were added to the homogeneous solution, which was then heated to reflux (81° C.). After 6 hours, the excess tetramethyldisiloxane and toluene were removed by distillation, the residue was taken up twice in toluene and dried by distillation. The cholesteryl 4-(3-(1, 1,3,3-tetramethyldisiloxanyl)propoxy)benzoate which remained was dissolved in 150 ml of anhydrous toluene, and a solution of 0.12 mole of allyl methacrylate in 50 ml of anhydrous toluene was added at 20° C. The solution was warmed at 60° C. for 1 hour with stirring. The toluene solution of the product was concentrated by evaporation, and the product was separated by addition of acetone at low temperature. Repeated reprecipitation gave a viscous, opaque liquid. The following phase behavior was determined on this product: Sg 58 Sa 116 i Owing to the high viscosity of the smectic phase, the product could not be homogeneously aligned between glass plates by applying shear forces. On warming, a sample sheared between glass plates exhibited no reflection color.

What is claimed is:

1. A liquid-crystalline siloxane of the formula $$Y^1-(SiR_2O)_\pi-SiR_2-Y^2 \quad (I)$$

in which
- $Y^1$ is a mesogenic group which is bonded to a silicon atom of the (SiR$_2$O) group by an alkyl or alkenyl radical,
- $Y^2$ is an organic radical containing at least one polymerizable group having at least one ethylenically unsaturated double bond and at least one divalent cyclic group,
- R is a $C_1$- to $C_3$-alkyl radical, and
- $\pi$ is an integer having a value of from 1 to 5.

2. A liquid-crystalline siloxane as claimed in claim 1, wherein mesogenic group containing $Y^1$ conforms to the formula $$-D-(X^1{}_a-A^1{}_b-A^2{}_c)_d-Z_e-(-X^2{}_f-A^3{}_g-A^4{}_h-)_i-A^5{}_k \quad (II),$$

in which
- D is a divalent hydrocarbon radical of the formula $C_nH_m$ which is unsubstituted or substituted by halogen atoms and in which one or more non-adjacent methylene units may be replaced by $X^1$,
- n is an integer having a value of from 1 to 20
- m is a non-negative number having a value of (2n) or (2n-2),
- $X^1$ and $X^2$ are each divalent radicals from the group consisting of —O—, —COO—, —CONH—, —CO—, —S—, —C≡C—, —CH=CH—, —CH$_2$—CH$_2$—, —CH=N—, —N=N— and —N=N(O)—,
- $A^1$, $A^2$, $A^3$ and $A^4$ are each divalent radicals, 1,4-phenylene, 1,4-cyclohexylene radicals, substituted arylenes having 6 to 10 carbon atoms and substituted cycloalkylenes having 6 to 10 carbon atoms,
- Z are each divalent to tetravalent benzene-1,4-cyclohexane or 1,3-cyclopentane radicals,
- $A^5$ are each saturated or olefinically unsaturated alkyl, alkoxy or cycloalkyl radicals having 1 to 16 carbon atoms, steroid radicals, halogen atoms, hydrogen atoms, hydroxyl, nitrile and trialkylsiloxy groups whose respective alkyl radicals have 1 to 8 carbon atoms,
- a, b, c, d, f, g, h, i and k are each integers having a value of 0, 1, 2 or 3, the sum a+b+c+d+e+f+g+h+i+k is at least 2 and the sum of d and i is at most 4, and
- e is a number having a value of 0 or 1, with the proviso that no two oxygen atoms in $Y^1$ are directly bonded to one another.

3. A liquid-crystalline siloxane as claimed in claim 1, wherein the organic radicals $Y^2$ containing at least one polymerizable group and at least one divalent cyclic group conform to the formula $$-D-(X^1{}_a-B^1{}_b-B^2{}_c)_3-Z_e-(X^2{}_f-B^3{}_g-B^4{}_h-)_i-A^5{}_k \quad (V)$$

in which
- $B^1$, $B^2$, $B^3$ and $B^4$ are as defined for the radicals $A^1$, $A^2$, $A^3$, $A^4$ and D,
- D, $X^1$, $X^2$, Z, $A^5$, a, b, c, d, f, g, h, i, k and e are as defined above under formula II, where the sum b+c+e+g+h is at least 1, with the proviso that no two oxygen atoms in $Y^2$ are directly bonded to one another and at least one ethylenically unsaturated double bond is present.

4. A liquid-crystalline siloxane as claimed in claim 1, wherein $\pi$ has the value of 1.

5. A process the preparation of a liquid-crystalline siloxane as claimed in claim 1, wherein a compound of the formula $$Y^1(SiR_2-O)_\pi-SiR_2H \quad (X),$$

in which
- $Y^1$, R and $\pi$ are as defined above, is reacted with an alkene and/or alkyne containing a polymerizable group and at least one divalent cyclic group in the presence of a known hydrosilylation catalyst.

6. A liquid-crystalline polyorganosiloxane obtainable by polymerization of a liquid-crystalline siloxane as claimed in claim 1.

7. Optical filters and reflectors containing polymerized liquid-crystalline siloxane as claimed in claim 6.

* * * * *